United States Patent [19]
Kopf

[11] 3,994,297
[45] Nov. 30, 1976

[54] OPHTHALMIC INSTRUMENT

[76] Inventor: J. David Kopf, 10369 Pinyon Ave., Tujunga, Calif. 91042

[22] Filed: Dec. 9, 1974

[21] Appl. No.: 530,879

[52] U.S. Cl. .............................. 128/276; 128/305
[51] Int. Cl.² ................... A61M 7/00; A61B 17/32; A61F 9/00
[58] Field of Search ..................... 128/2 B, 276, 305

[56] References Cited
UNITED STATES PATENTS

| 3,517,669 | 6/1970 | Buono et al. | 128/276 |
| 3,732,858 | 5/1973 | Banko | 128/305 |
| 3,776,238 | 12/1973 | Peyman et al. | 128/305 |
| 3,815,604 | 6/1974 | O'Malley et al. | 128/305 |

FOREIGN PATENTS OR APPLICATIONS 437,932   11/1926   Germany ........................... 128/305

OTHER PUBLICATIONS

Peyman et al., "Experimental Vitrectomy," in Arch. Ophthal. 86: 548 – 551, 1971.

Primary Examiner—Channing L. Pace

[57] ABSTRACT

An improved ophthalmic instrument for removing vitreous and the like from the eye is provided having a smooth, unobstructed exterior surface for easy handling. The air pressure connection, vacuum connection and saline infusion connection are made through the end wall of the cap of the device.

5 Claims, 3 Drawing Figures

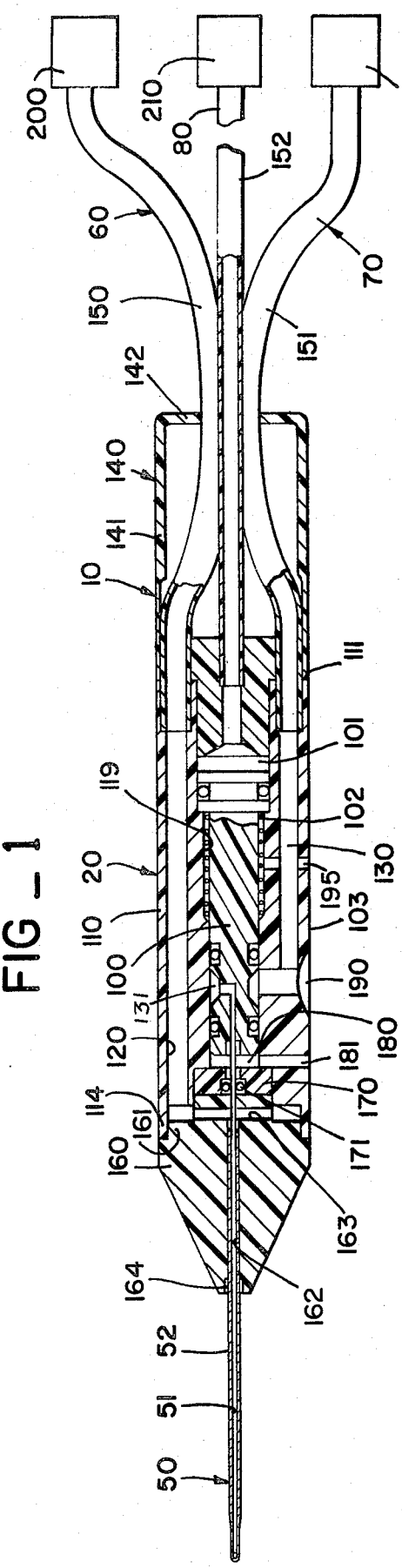
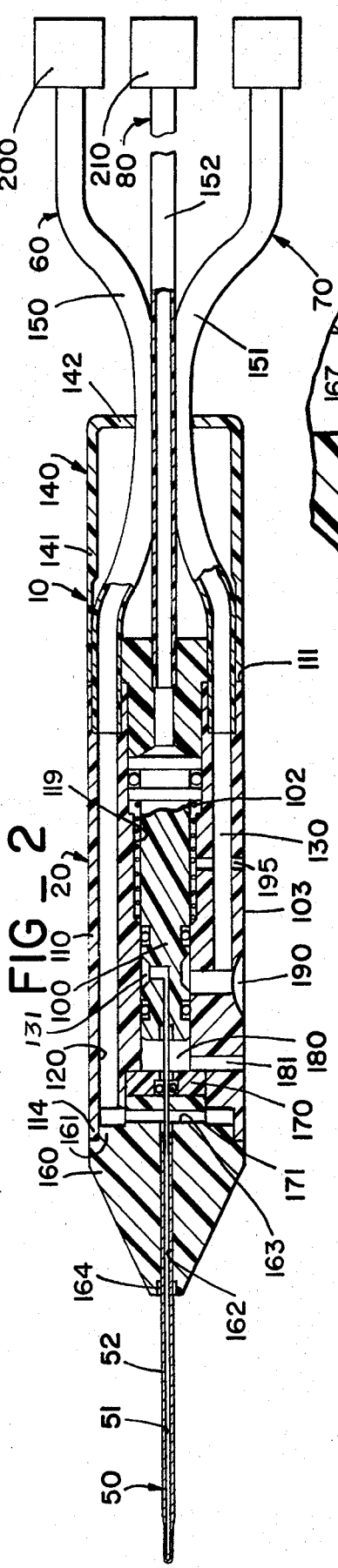

OPHTHALMIC INSTRUMENT

This invention relates to an ophthalmic instrument for surgically removing vitreous and the like from the eye and for replenishing the removed vitreous and the like with saline solution. The invention more specifically is directed to an improvement in such a surgical instrument to render the instrument easier to handle than the instruments of the prior art.

The prior art instruments include that shown in the May 1973 issue of the "American Journal of Ophthalmology" at page 776 and the related discussion. Another machine of this type is shown in the O'Malley U.S. Pat. No. 3,815,604 for Apparatus for Intraocular Surgery which issued on June 11, 1974. Still another instrument of this general type is shown in application Ser. No. 174,349 for "Ophthalmic Instrument" filed Aug. 24, 1971.

None of the prior art disclosed above or otherwise known to applicant provides an instrument which is as easily handled by a surgeon as that described herein. The instrument described herein may be made of lightweight molded plastic such as delrin. The assembly contains numerous internal passageways which in combination render the exterior surface of the instrument unobstructed and therefore extremely easy to handle.

A primary object of this invention is to provide an ophthalmic instrument for removing vitreous and the like from the eye which is extremely easy to handle.

A further object of this invention is to provide an ophthalmic instrument for removing vitreous and the like from the eye which is very simple in design and which is disposable.

Further objects and advantages of the invention become apparent from the following description of the preferred embodiment and the drawings wherein:

FIG. 1 is an elevational view in section of the invention;

FIG. 2 is a side elevational view in section of the invention and;

FIG. 3 is an elevational view in section of the end of the cutting means of the instrument.

Referring to FIG. 1, an ophthalmic instrument is shown, referred to generally as 10. The instrument contains the following components, which, in and of themselves, are not a part of this invention: a body 20, cutting means 50, infusion means 60, vacuum means 70 and pneumatic driving means 80.

The instrument functions as follows. Cutting means 50 has an inner tube 51 slidably carried in an outer tube 52. As shown best in FIG. 3, as inner tube 51 reciprocates in outer tube 52, material to be excised enters port 53, is sheared off by inner tube 51 and is removed through the interior portion of tube 51 by vacuum means 70. Saline is infused back into the eye along the space 55 between the inner tube 51 and outer tube 52 and thence through port 54 in outer tube 52. Inner tube 51 is rigidly carried by piston 100. Piston 100 is driven by pneumatic driving means 80 which provides pulses of compressed air from a source 210 into chamber 101 which moves piston 100 to the left, compressing spring 102. Spring 102 returns piston 100 to the position shown in FIG. 2.

The specific components referred to above do not form a part of this invention, but provide the environment for the instant invention.

The instant invention is directed towards the arrangement of the components of body 20 and the internal passageways and components thereof. This arrangement of passageways and components provides an instrument which is extremely easy to handle for performing the delicate surgeries involved.

An elongated case 110 is provided which is of molded plastic. Case 110 has an open end defined by a flat back mating edge surface 111 and has also an unobstructed, smooth exterior surface 103. An infusion passageway 120 is provided internally in case 110 and communicates cutting means 50 with the back mating surface 111.

Vacuum passageway 130 is also formed internally in case 110 communicating cutting means 50 with back mating surface 111.

Cap means 140 connects to back mating surface 111 as by gluing. Cap means 140 has side walls 141 and an end wall 142. The exterior surface of side walls 141 is smooth and unobstructed and forms a continuous surface with the exterior surface of case 110.

Thus, the combination of case 110 and cap means 140 forms a generally cylindrical body having a smooth, continuous and unobstructed exterior surface.

Connecting means 150, 151 and 152 extend through end wall 142 and communicate said infusion passageway 120, vacuum passageway 130 and cutting means 50 to said infusion means 60, vacuum means 70 and pneumatic driving means 80, respectively. Cutting means 50 is connected to pneumatic driving means 80 through piston 100. Connecting means 150, 151 and 152 are plastic flexible tubes.

A saline reservoir 200 is detachably connected to connecting means 150. Vacuum source 220 is detachably connected to connecting means 151, and compressed air source 210 is detachably connected to connecting means 152. At the conclusion of surgery, the instrument 10 is detached from reservoir 200, compressed air source 210 and vacuum source 220 and is disposed of.

Outer tube holding means 160 is provided which connects to the front of case 110. This connection is achieved by gluing shoulder 161 in the end 114 of case 110. Outer tube holding means 160 holds outer tube 52 in a stationary position relative to case 110. This is done by gluing outer tube 52 in a bore 162 in holding means 160.

An infusion bore 163 is provided in holding means 160 extending transversely therethrough, which communicates with passageway 120 and allows saline solution to enter the space 55 as shown by arrows 167 (FIG. 3) and flow through port 54 into the eye. Outer tube 52 extends into bore 162 to within about 1/16 inch of infusion bore 163 as shown in the right hand section of FIG. 3. A counterbore 164 is provided in the tip of outer tube housing means 160 in which epoxy glue is applied to help secure outer tube 52 to holding means 160.

Inner tube sealing means 170 is also provided. Inner tube sealing means 170 is mounted in the forward end of case 110 for sealing infusion passageway 120 with respect to piston 100. Inner tube sealing means 170 contains an O-ring which slidably engages inner tube 51. Inner tube 51 extends through outer tube housing 160 into piston 100 and terminates at port 131. Inner tube 51 is supported by piston 100 to which it is rigidly connected by gluing.

Cavity 180 between inner tube sealing means 170 and piston 100 is vented to atmosphere by passageway 181. This avoids compression of the air trapped between inner tube bearing means 170 and piston 100.

Recess 119 is formed in case 110 and houses spring 102. Recess 119 is vented to atmosphere by vent means 195 to avoid compression of air in recess 119.

Vacuum passageway 130 is vented to atmosphere by vent means 190. Vent means 190 is located in a different radial plane from vent 195 so that vent 195 cannot communicate with vacuum passageway 130. This enables the surgeon to shut off the vacuum suction by merely opening vent 190 as by lifting his finger therefrom and allowing the vacuum to work against the ambient atmosphere.

I claim:

1. In an ophthalmic instrument for removing vitreous and the like from the eye and for replenishing the removed vitreous and the like with saline solution having a body, cutting means connected to said body, infusion means connected to said body for infusing saline solution through said cutting means into the eye, vacuum means connected to said body for generating a vacuum in said cutting means for removing material excised from the eye and pneumatic driving means connected to said body for driving said cutting means, the improvement wherein said body comprises:
    an elongated case having an open end defined by a back mating edge and a smooth, unobstructed exterior surface,
    an infusion passageway formed internally in said case communicating said cutting means with said back mating edge,
    a vacuum passageway formed internally in said case communicating said cutting means with said back mating edge,
    cap means connected to said back mating edge, said cap means having side walls and an end wall, the exterior surface of said side walls being smooth and unobstructed and forming a continuation of the exterior surface of said case, and
    connecting means extending through said end wall of said cap means for communicating said infusion and vacuum passageways to said infusion and vacuum means respectively, and for communicating said pneumatic driving means to said cutting means.

2. The improvement of claim 1 wherein said cutting means comprises inner and outer tubes, said inner tube rigidly carried by a piston and slidably mounted in said outer tube, and wherein said body further comprises:
    outer tube holding means connected to the front of said case for holding said outer tube in a stationary position relative to said case.

3. The improvement of claim 2 wherein said body further comprises:
    inner tube sealing means mounted in the forward end of said case for sealing said infusion passageway with respect to said piston.

4. The improvement of claim 3 wherein said case has a cavity between said piston and said inner tube sealing means and wherein a vent is provided between said cavity and the atmosphere.

5. The improvement of claim 3 wherein said vacuum passageway is vented to atmosphere.

* * * * *

UNITED STATES PATENT OFFICE
CERTIFICATE OF CORRECTION

Patent No. 3,994,297     Dated November 30, 1976

Inventor(s) J. David Kopf

It is certified that error appears in the above-identified patent and that said Letters Patent are hereby corrected as shown below:

Column 3, line 2, "bearing means" should be "sealing means".

Signed and Sealed this

Eighth Day of March 1977

[SEAL]

Attest:

RUTH C. MASON
*Attesting Officer*

C. MARSHALL DANN
*Commissioner of Patents and Trademarks*